United States Patent
Jackowski et al.

(10) Patent No.: US 6,565,571 B1
(45) Date of Patent: May 20, 2003

(54) ANTERIOR OSTEOSYNTHESIS PLATE FOR LUMBAR VERTEBRAE OR SACRAL LUMBAR VERTEBRA AND INSTRUMENT FOR POSITIONING SAME

(75) Inventors: Andre Jackowski, Birmingham (GB); Vincent Fiere, Lyons (FR); Charles Billot, Ermont (FR); Philippe Lemaitre, Alfortville (FR)

(73) Assignee: Scient'X, Paris (FR)

( * ) Notice: Subject to any disclaimer, the term of this patent is extended or adjusted under 35 U.S.C. 154(b) by 0 days.

(21) Appl. No.: 09/890,110

(22) PCT Filed: Oct. 19, 1999

(86) PCT No.: PCT/FR99/02543

§ 371 (c)(1),
(2), (4) Date: Jul. 26, 2001

(87) PCT Pub. No.: WO00/22999

PCT Pub. Date: Apr. 27, 2000

(30) Foreign Application Priority Data

Oct. 19, 1998 (FR) .............................. 98 13225

(51) Int. Cl.[7] .............................................. A61B 17/70
(52) U.S. Cl. ........................................... 606/69; 606/61
(58) Field of Search ............................ 606/61, 69–71, 606/99

(56) References Cited

U.S. PATENT DOCUMENTS

| 3,741,205 A | * | 6/1973 | Markolf et al. | |
|---|---|---|---|---|
| 4,503,848 A | * | 3/1985 | Casper et al. | |
| 5,041,113 A | * | 8/1991 | Biedermann et al. | 606/61 |
| 5,423,826 A | * | 6/1995 | Coates et al. | 606/96 |
| 5,470,333 A | * | 11/1995 | Ray | 606/61 |
| 5,603,713 A | | 2/1997 | Aust et al. | |
| 5,616,144 A | | 4/1997 | Yapp et al. | |
| 5,785,712 A | * | 7/1998 | Runciman et al. | 606/69 |
| 5,904,683 A | * | 5/1999 | Pohndorf et al. | 606/61 |
| 6,017,345 A | * | 1/2000 | Richelsoph | 606/70 |
| 6,045,552 A | * | 4/2000 | Zucherman et al. | 606/61 |
| 6,159,213 A | * | 12/2000 | Rogozinski | 606/70 |

OTHER PUBLICATIONS

H.S. An et J.M. Cotler (Eds.): "Spinal Instrumentation": 1992, Williams & Wilkins; XP002108102 22396; p. 379–p. 396.

* cited by examiner

Primary Examiner—Ralph A. Lewis
(74) Attorney, Agent, or Firm—Ladas & Parry

(57) ABSTRACT

The invention relates to an anterior osteosynthesis plate for lumbar-lumbar or lumbar-sacral vertebrae, the plate being of the type comprising:

an elongate body:
  adapted to cover of the anterior portions of two consecutive vertebrae;
  possessing an anterior face (6) and an opposite posterior face (7);
  presenting end zones that are interconnected by a connection zone (11); and
  provided with two through holes for anchoring screws.

According to this invention, the posterior face (7) of the plate presents a bearing surface (12, 13), which bearing surface is designed to come into contact with the anterior surface (3) of the corresponding vertebra, the bearing surfaces (12, 13) being firstly inclined to define an obtuse angle (α) between them in the sagittal plane (S) matching the relative angle between the anterior portions of the two vertebrae, and secondly being interconnected in the connection zone by a concave extension (17) such that at least the posterior face (7) of the body presents a profile that is concave in the sadittal plane.

11 Claims, 3 Drawing Sheets

ANTERIOR OSTEOSYNTHESIS PLATE FOR LUMBAR VERTEBRAE OR SACRAL LUMBAR VERTEBRA AND INSTRUMENT FOR POSITIONING SAME

TECHNICAL FIELD

The subject matter of the invention relates to the general technical field of intervertebral connection devices for correcting weakening of the vertebrae or poor posture of the spinal column by providing stabilization about a longitudinal axis and on the antero-posterior plane.

More precisely, the subject matter of the invention relates to lumbar-lumbar or lumbar-sacral vertebrae connection devices for fixing to the anterior faces of said vertebrae.

PRIOR ART

Numerous types of intervertebral connection device are known in the state of the art. Thus, in particular from French design application No. 96/7390, an anterior osteosynthesis plate for lumbar vertebrae is known comprising an elongate body adapted to cover at least part of the anterior portions of two consecutive vertebrae. The elongate body possesses an anterior face and a posterior face opposite thereto for pressing against the anterior faces of the vertebrae. The elongate body has end zones interconnected by a connection zone, and each end zone is hook-shaped. Each end zone is provided with a through hole for a screw that is to be anchored in a vertebral body.

Such a plate makes it possible to interconnect two vertebrae after reestablishing the intervertebral space. Such a plate prevents the vertebrae from turning about the longitudinal axis and tilting in the antero-posterior plane, and it enables the vertebrae to be stabilized by encouraging arthrodesis thereof.

The above-described anterior lumbar plate presents a certain number of drawbacks. Thus, it appears that each hook-shaped end portion of the plate is for anchoring to the anterior edges of the plates of the vertebral bodies. Unfortunately, it must be understood that from one patient to another, firstly the anterior edges of the plates are of varying profiles, and secondly the size of the intervertebral space varies. As a result, it is difficult to position such a plate correctly, even when plates are available in a set of plates having different dimensions and profiles. In addition to the need to have a wide variety of plates, it should also be observed that poor positioning of such a plate degrades the quality of intervertebral connection, and consequently degrades intervertebral stability during bone fusion.

SUMMARY OF THE INVENTION

The object of the invention is to remedy the above-specified drawbacks by proposing an anterior osteosynthesis plate for lumbar-lumbar or lumbar-sacral vertebrae, that is designed to present great adaptability during installation, independently of the dimensions presented by the intervertebral space and of the dimensions and/or profile of the vertebral bodies to which such a plate is to be fixed.

To achieve this object, the invention provides an anterior osteosynthesis plate for lumbar-lumbar or lumbar-sacral vertebrae, the plate being of the type comprising:

an elongate body:
  adapted to cover at least part of the anterior portions of two consecutive vertebrae;
  possessing an anterior face and an opposite posterior face designed to be pressed against the anterior faces of the vertebrae;
  presenting end zones that are interconnected by a connection zone; and
  provided with two through holes for anchoring screws, each formed in a respective one of the end zones.

According to the invention, the posterior face of the body of the plate presents a bearing surface in each end zone, which bearing surface is designed to come into contact with the anterior face of the corresponding vertebra, the bearing surfaces being firstly inclined to define an obtuse angle between them in the sagittal plane matching the relative angle between the anterior portions of the two vertebrae, and secondly being interconnected in the connection zone by a concave extension such that at least the posterior face of the body presents a profile that is concave in the sagittal plane.

According to another characteristic of the invention, the through holes of the plate are constituted by bores formed in such a manner that their axes define respective angles of inclination in the sagittal plane relative to the planes in which the associated bearing surfaces extend, so that said axes diverge from each other going away from the body.

This characteristic makes it possible to obtain screw anchoring in diverging directions suitable for taking up the forces that might act on the plate.

Various other characteristics appear from the following description given with reference to the accompanying drawings which show embodiments and implementations of the invention as non-limiting examples.

BEST MANNER OF PERFORMING THE INVENTION

Figure 3:
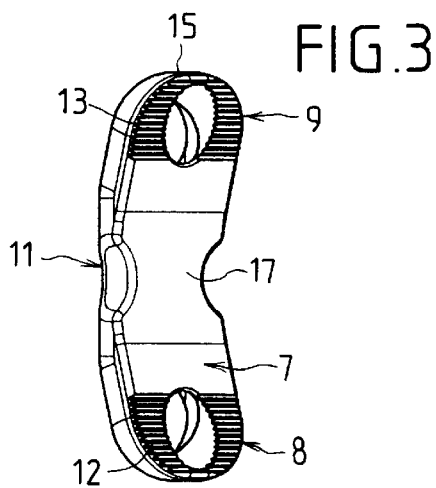
FIG. 3 is a three-quarter rear view of an anterior plate constituting the first embodiment.
Figure 4:
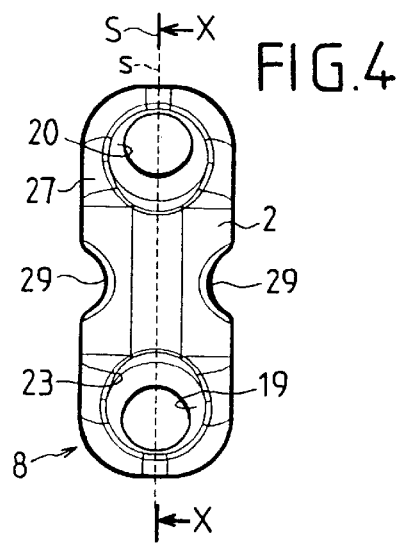
FIG. 4 is a front view of a plate constituting the first embodiment.

FIGS. 1 to 5 show a first embodiment of an anterior osteosynthesis plate I for preventing two lumbar vertebrae from moving relative to each other, e.g. $L_4$ and $L_5$. The plate I of the invention is in the form of an elongate body 2 of substantially parallelepipedal shape possessing a longitudinal axis s lying on a longitudinal plane of symmetry S coinciding with the sagittal plane of the plate (FIG. 4). The length of the body 2 is adapted to cover, at least in part, the anterior faces or portions 3 of the bodies 4 of two consecutive vertebrae, and specifically $L_4$ and $L_5$ in the example shown.

The body 2 has an anterior face 6 and a posterior face 7 opposite from the anterior face 6. The posterior face 7 is for pressing against the anterior faces 3 of the vertebral body 4. The body 2 has two end zones 8 and 9 interconnected by a central connection zone 11.

Figure 5:
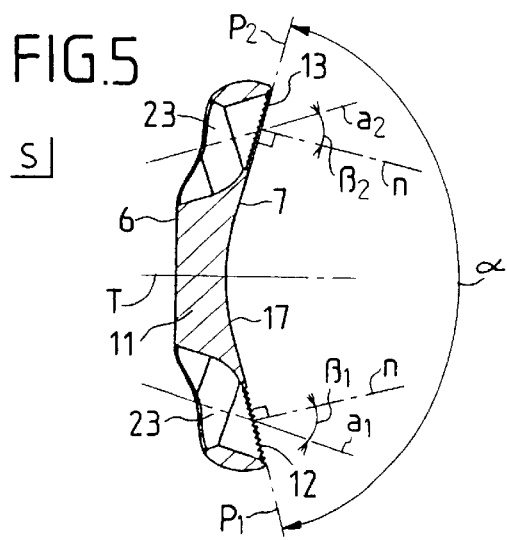
FIG. 5 is an elevation view in section substantially on line X—X of FIG. 4.

In accordance with the invention, in each of its end zones 8 and 9, the posterior face 7 of the body 2 presents a respective bearing surface 12, 13 for coming into contact with the anterior face of a vertebra. Each bearing surface 12, 13 extends in a respective plane $P_1$, $P_2$ perpendicular to the sagittal plane or plane of symmetry S of the plate 2. In FIG. 5, the sagittal plane S is considered as coinciding with the plane of the sheet of paper. According to a characteristic of the invention, the bearing surfaces 12 and 13 are inclined in the sagittal plane S so as to define between them an obtuse angle α. As can be seen more clearly in FIG. 5, the planes $P_1$ and $P_2$ define between them an obtuse angle α which, in this embodiment, lies in the range 140° to 160°, and is preferably about 150°. The value of the obtuse angle α matches the angle formed between the front portions 3 of the two vertebrae $L_4$, $L_5$. In this embodiment, the bearing surfaces $P_1$, $P_2$ extend symmetrically to each other so that the planes $P_1$, $P_2$ in which the bearing surfaces extend form a half-angle α with the transverse plane T perpendicular to the longitudinal axis s.

In a preferred implementation and as can be seen more clearly in FIG. 3, each bearing surface 12, 13 is provided with roughnesses 15 to encourage anchoring between the plate 2 and the anterior portions 3 of the vertebrae. The presence of roughness 15 also facilitates installation of the plate 2 on an anterior portion 3 while it is being positioned thereon. In the example shown, the roughnesses 15 are constituted by a succession of ribs extending in a direction perpendicular to the longitudinal axis of symmetry s. Naturally, it is clear that the roughnesses 15 could have a variety of profiles other than transverse ribs. Also preferably, the grooves begin to be provided at the end edges of the body 2 and they cover at least part of the area of each of the bearing surfaces 12, 13.

As can be seen more clearly in FIGS. 3 and 5, the bearing surfaces 12, 13 are interconnected via the connection zone 11 by means of a concave extension 17 so that at least the posterior face 7 of the body 2 presents a profile that is concave in the sagittal plane S.

According to another preferred characteristic, the plate 2 has through holes 19 and 20 formed respectively through each of its end zones 8 and 9. These through holes 19 and 20 open out in the anterior face 6 and in the posterior face 7 within the bearing surfaces 12, 13. According to an advantageous characteristic of the invention, these through holes 19 and 20 constitute bores so that their axes $a_1$, $a_2$ define respective angles of inclination $\beta_1$ and $\beta_2$ in the sagittal plane S relative to the normal n to the extension planes $P_1$, $P_2$ of the associated bearing surfaces so that they diverge from each other going away from the body 2. In the first embodiment, the angles $\beta_1$ and $\beta_2$ are identical. Each bore 19, 20 preferably presents an angle of inclination $\beta_1$, $\beta_2$ in the sagittal plane that lies in the range 28° to 38°, and is preferably about 33°.

The bores 19, 20 serve to pass and position anchoring screws 22 which, when inserted in the bores, are located on the axes $a_1$ and $a_2$. According to a preferred characteristic, each bore 19, 20 opens out into the anterior face 6 of the body 2 via a housing 23 for positioning the head of an anchoring screw. Naturally, each housing 23 has an opening of section that is suitable for enabling anchoring screws to be inserted from the anterior face 6 along the directions defined by the axes $a_1$ and $a_2$ of the bores.

According to a preferred characteristic, the body 2 presents in the sagittal plane S and at least on the longitudinal axis of symmetry s, thickness that is substantially constant. In other words, and as can be seen more clearly in FIG. 5, the body 2 has an anterior face 6 whose profile is generally concave analogous to the profile of the posterior face 7. More precisely, in the connection portion 11, the anterior face 6 is plane and extends up to the edges of the housings 23. At the housings 23, the anterior face 6 presents a profile that is substantially parallel to the bearing surfaces 12, 13. In a preferred embodiment, the anterior face 6 presents over its entire periphery a convex extension 27 running into the lateral faces 28 of the body interconnecting the anterior and posterior faces 6 and 7. The lateral faces 28 are preferably interconnected by rounded surfaces. As a result, the body 2 is rounded in shape from its anterior face 6 to its posterior face 7 without any roughnesses or projecting corners. Such a rounded profile for the body 2 makes it possible to avoid any risk of lesion or injury, in particular to the nerves, blood vessels, or tissues located in the vicinity.

According to a preferred characteristic, the body 2 presents two notches 29 in its opposite lateral faces 28 level with the connection zone 11, which notches are for co-operating with an instrument for positioning the plate.

Figure 6:
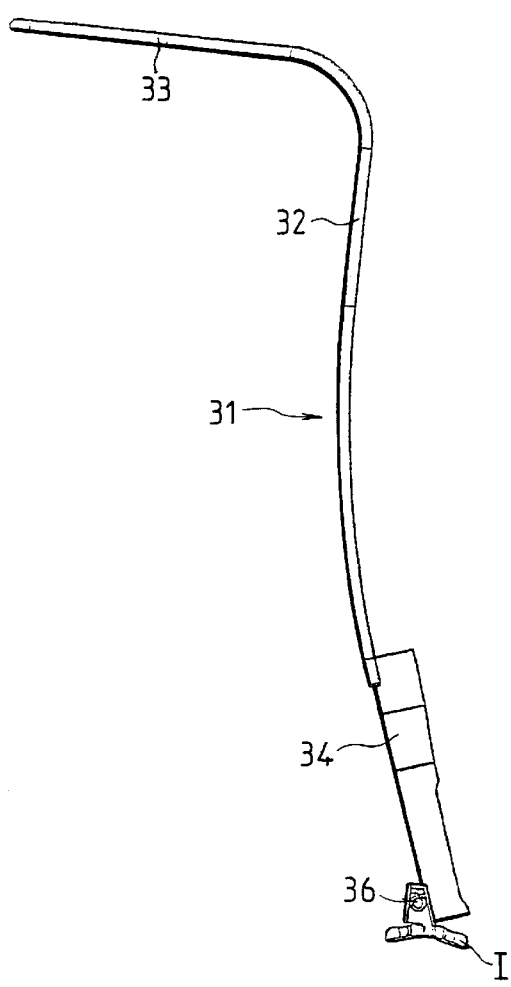
FIG. 6 is an elevation view of an instrument enabling a plate of the invention to be put into place.
Figure 8:
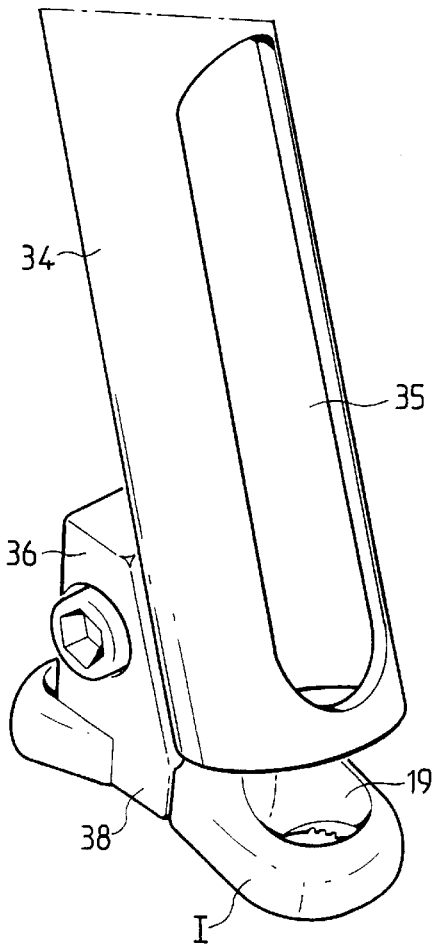
FIG. 8 is a perspective view showing a detail characteristic of the implementation of the instrument.
Figure 7:
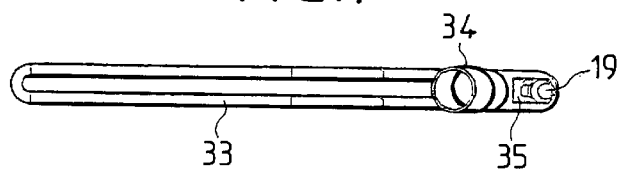
FIG. 7 is a plan view of the instrument shown in FIG. 6.
Figure 9:
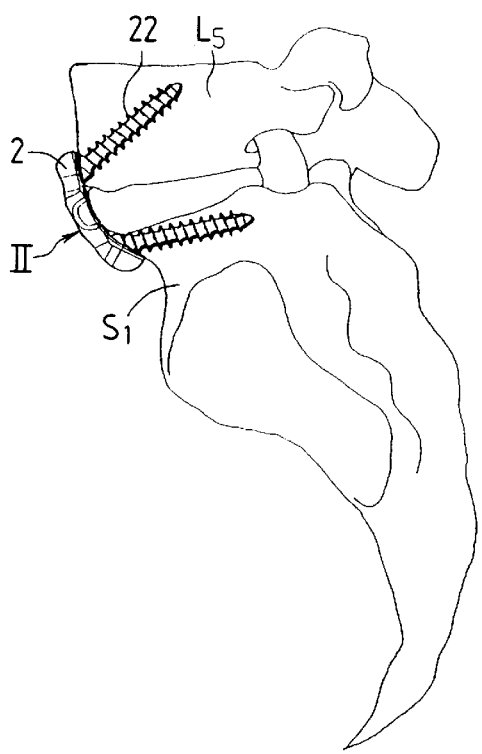
FIG. 9 is a diagrammatic view showing a second embodiment of an anterior plate for making a connection between the sacral and the lumbar vertebrae.
Figure 10:
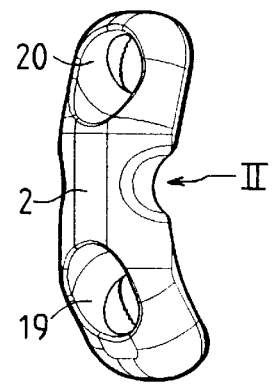
FIG. 10 is a three-quarter front view of a plate constituting the second embodiment.
Figure 11:
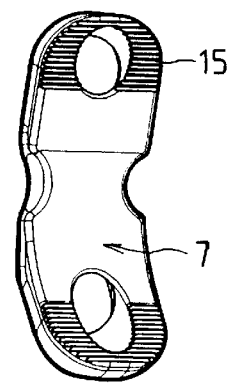
FIG. 11 is a three-quarter rear view of a plate constituting the second embodiment.
Figure 13:
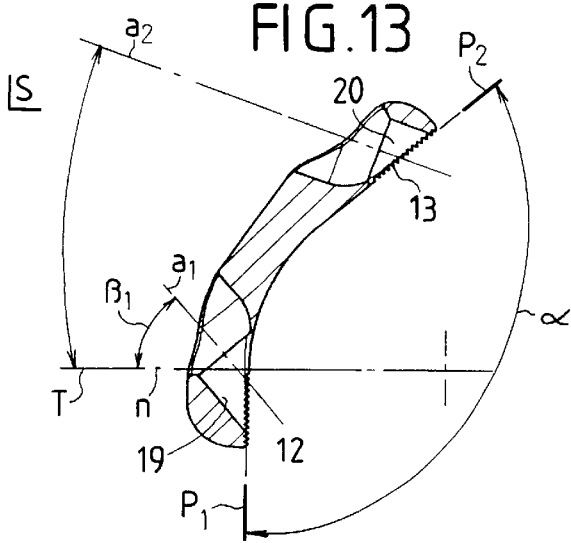
FIG. 13 is an elevation view in section taken substantially on line X—X in FIG. 12.
Figure 12:
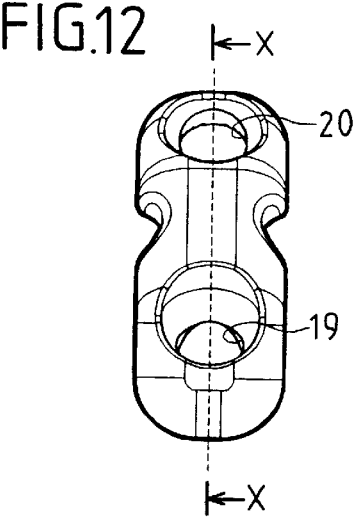
FIG. 12 is a front view of a plate constituting the second embodiment.

By way of example, FIGS. 6 to 8 show an instrument 31 enabling an osteosynthesis plate I of the invention to be positioned. Such an instrument 31 comprises a handle 32 shaped to present a grip 33 extending substantially perpendicularly to the main direction in which the handle extends. The end of the handle 32 remote from its end forming the grip 33 is provided with a guide tube 34 for tools (not shown but known per se) that perform the various operations involved with anchoring the screws 22. In its lower portion and along a determined axial length, the tube 34 is provided with a sighting slot 35 extending over the front portion of the tube 34 remote from the grip 33 of the instrument. In its bottom region and diametrically opposite from the slot 35, the tube 34 has a shoe 36 for holding a plate I. As can be seen more clearly in FIGS. 7 and 8, in the plate-gripping position, the projection of the longitudinal sighting slot 35 coincides at least in part with the bottom through section of the guide tube which is to be caused to extend on the same axis as one of the bores 19, 20 of the body of the plate I held by the shoe 36. The shoe 36 preferably holds the plate I in position via two studs 38 for engaging by elastic deformation in the notches 29 of the plate I. It should be observed that the plate I is held in a stable reference position by the shoe 36 insofar as the end opposite from that superposed with the tube 34 bears against the shoe 36.

Implementation of an osteosynthesis plate of the invention stems directly from the above description.

Before fitting a plate to the vertebrae of a patient, the portions of the anterior faces 3 of the vertebrae that are to receive the bearing surfaces 12 and 13 are prepared so as to present a flat on each vertebral body. In order to install the plate I on the vertebrae as prepared in this way, the plate is mounted by being snap-fastened to the guide shoe 36 of the instrument 31. Because of the presence of the longitudinal slot 35 whose projection coincides with one of the bores 19, 20 formed in the plate, the operator can see the conventional operations of putting screws 32 into place in the vertebrae. It should be observed that during these operations, the tools are guided in displacement by the tube 34. In this respect, the relative angle between the guide tube 34 and the gripping shoe 36 is selected so that the axis of the tube 34 coincides with the axis $a_1$, $a_2$ with one of the bores while the plate 2 occupies its stable position bearing against the shoe. This ensures that the anchoring screws 22 are properly positioned since they are well guided by the directed bores 19, 20. It should be considered that the presence of the roughnesses 15 which prevents the plate I from slipping make it easier to put the plate I into place.

After one of the anchoring screws 22 has been put into place, the instrument 31 is separated from the plate 2 merely by applying traction, and after being turned through 180° it is snap-fastened back onto the plate so as to make it possible to perform installing operations on the other anchoring screw 22.

Figure 1:
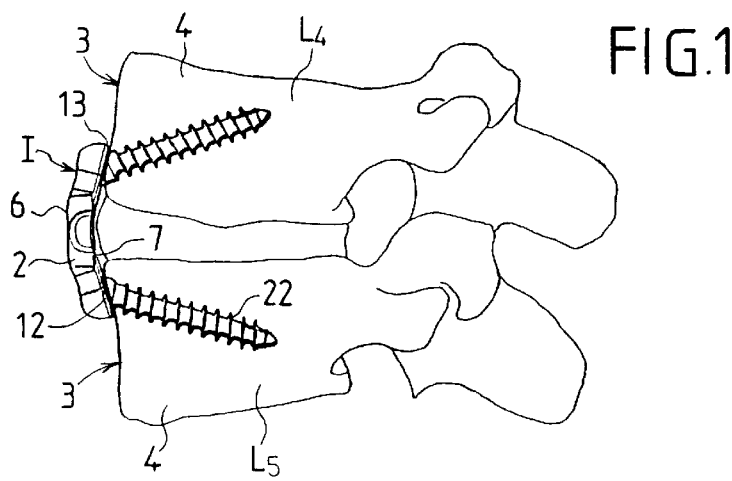
FIG. 1 is a diagrammatic view of an embodiment of an anterior osteosynthesis plate of the invention mounted on lumbar vertebrae.
Figure 2:
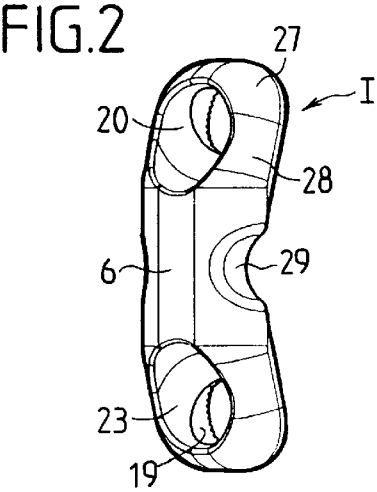
FIG. 2 is a three-quarter front view of a plate constituting the first embodiment as shown in FIG. 1 for lumbar vertebrae.

As can be seen from FIG. 1, after assembly, the plate 1 is in contact via its bearing surfaces 12 and 13 with flats made on the vertebral body 4. This provides plane contact between each bearing surface 12, 13 and the anterior face 3 of the vertebral body 4. The quality of such contact associated with the anchoring screws 22 being mounted so as to diverge makes it possible to take up forces and stabilize the vertebrae relative to each other. It should be observed that the connection zone 11 of the plate has a concave extension 17 overlying the intervertebral space. The clearance left at this location by the plate I allows it to adapt to the various shapes of intervertebral space that are to be found.

Susceptibility of Industrial Application

In the embodiment described above, the osteosynthesis plate is particularly suited for interconnecting two lumbar vertebrae. Naturally, the subject matter of the invention can also be applied to an osteosynthesis plate for installing between a lumbar vertebra and the sacral vertebra, i.e. $L_5$-$S_1$. FIGS. 9 to 13 show a second embodiment of an osteosynthesis plate II of the invention that is suitable for lumbar-sacral vertebrae interconnection.

It should be observed that elements in common between the plate II and those described for the first embodiment are given the same references. In this second embodiment, the bearing surfaces 12 and 13 of the plate are no longer symmetrical to each other about the transverse axis T. As can be seen more clearly in FIG. 13, the two bearing surfaces 12, 13 are inclined relative to each other in the sagittal plane S to define an angle a that matches the angle to be found between the anterior portions of the two vertebrae $L_5$-$S_1$. This obtuse angle α lies in the range 120° and 140°, and is preferably about 130°. In addition, in the sagittal plane, the bore 19 has an angle of inclination $\beta_1$ lying in the range 45° to 55°, and preferably about 50°, measured between the normal n to the plane $P_1$ and the axis $a_1$ of the bore 19. Similarly, the bore 20 presents an angle of inclination $\beta_2$ in the sagittal plane lying in the range 15° to 25°, and preferably about 20°, taken between the normal n to the bearing surface 12 and the axis $a_2$ of the bore 20.

The invention is not limited to the embodiments described and shown since numerous modifications can be made thereto without going beyond the ambit of the invention.

What is claimed is:

1. An anterior osteosynthesis plate for lumbar-lumbar or lumbar-sacral vertebrae, the plate being of the type comprising:

an elongated body:

adapted to cover at least part of the anterior portions of two consecutive vertebrae;

possessing an anterior face and an opposite posterior face designed to be pressed against the anterior faces of the vertebrae;

presenting first and second end zones that are interconnected by a connection zone; and provided with two through holes for anchoring screws, each formed in a respective one of the end zones;

wherein the posterior face of the body of the plate presents a first bearing surface in said first end zone, and a second bearing surface in said second end zone, each bearing surface being designed to come into contact with the anterior face of the corresponding vertebra, the bearing surfaces extending on separate planes and being firstly inclined to define an obtuse angle between said planes matching the relative angle between the anterior portions of the two vertebrae, and second being interconnected in the connection zone by a concave extension such that at least the posterior face of the body presents a profile that is concave in the sagittal plane; and wherein each bearing surface is provided with a roughnesses to encourage anchoring of the plate on the anterior portions of the vertebrae.

2. A plate according to claim 1, wherein said through holes have bores formed in such a manner that the bore axes define respective angles of inclination in the sagittal plane relative to the planes in which the associated bearing surfaces extend, so that said axes diverge from each other going away from the body.

3. A plate according to claim 2, wherein said bores each present an angle of inclination in the sagittal plane that is about 33° relative to the normal to the plane in which the associated bearing surface extends.

4. A plate according to claim 3, wherein the bearing surfaces extend symmetrically relative to each other, defining between them an obtuse angle of about 150°.

5. A plate according to claim 2, wherein said bores each present an angle of inclination in the sagittal plane respectively of about 50° and about 20° relative to the normal to the plane in which the associated bearing surface extends.

6. A plate according to claim 5, wherein the bearing surfaces are mutually offset in the sagittal plane by an obtuse angle of about 130°.

7. A plate according to claim 2, wherein each bore opens out in the anterior face of the body via a housing for positioning the head of an anchoring screw.

8. A plate according to claim 1, wherein the body has two notches in its connection zone for co-operating with an instrument for positioning the plate.

9. A plate according to claim 1, wherein the body presents a substantially constant thickness, at least in the sagittal plane.

10. A plate according to claim 9, wherein the body presents a convex extension and rounded lateral faces between the anterior face and the posterior face.

11. An instrument for positioning an osteosynthesis plate, the instrument comprising a handle provided with a tool guide tube, the tube being provided at a bottom end of the handle and in a diametrically opposed manner firsty with a shoe for gripping said plate and secondly with a longitudinal sighting slot with a projection which coincides at least in part with a bottom through section of the guide tube, said guide tube being intended to extend on the same axis as one of a first or second bores of a body of the plate, held by the shoe.

* * * * *